United States Patent
Young et al.

(10) Patent No.: US 10,463,829 B2
(45) Date of Patent: Nov. 5, 2019

(54) REGIONAL ANAESTHESIA INJECTION APPARATUS

(71) Applicant: The Queen Elizabeth Hospital King's Lynn NHS Foundation Trust, Norfolk (GB)

(72) Inventors: Peter Jeffrey Young, Norfolk (GB); Joseph Joachim Carter, Norfolk (GB); Emad Eldin Fahmy Fawzy, Norfolk (GB); John Edward Gibson, Norfolk (GB)

(73) Assignee: The Queen Elizabeth Hospital King's Lynn NHS Foundation Trust, Norfolk (GB)

( * ) Notice: Subject to any disclaimer, the term of this patent is extended or adjusted under 35 U.S.C. 154(b) by 0 days.

(21) Appl. No.: 15/315,706

(22) PCT Filed: May 29, 2015

(86) PCT No.: PCT/GB2015/051574
§ 371 (c)(1),
(2) Date: Dec. 1, 2016

(87) PCT Pub. No.: WO2015/185895
PCT Pub. Date: Dec. 10, 2015

(65) Prior Publication Data
US 2017/0095638 A1   Apr. 6, 2017

(30) Foreign Application Priority Data
Jun. 2, 2014 (GB) ..................... 1409795

(51) Int. Cl.
*A61M 19/00* (2006.01)
*A61M 5/145* (2006.01)
(Continued)

(52) U.S. Cl.
CPC .......... *A61M 19/00* (2013.01); *A61M 5/1456* (2013.01); *A61M 5/1723* (2013.01);
(Continued)

(58) Field of Classification Search
CPC .... A61M 19/00; A61M 5/1723; A61M 5/168; A61M 5/16854; A61M 2205/332
See application file for complete search history.

(56) References Cited

U.S. PATENT DOCUMENTS 7,449,008 B2 * 11/2008 Hochman .......... A61M 5/1456
604/67
2011/0257907 A1   10/2011 Kalpin
(Continued)

FOREIGN PATENT DOCUMENTS

KR    20090028086 A    3/2009
KR    20090028086A A   3/2009
(Continued)

*Primary Examiner* — Laura A Bouchelle

(57) ABSTRACT

A regional anesthesia injection apparatus comprising an injection volume determiner. The apparatus configured to determine a volume of a regional anesthetic injection into a target tissue; an injection pressure determiner configured to determine a pressure of the injection; and a controller coupled to the injection volume determiner and to the injection pressure determiner and configured to provide an injection signal to control injection of fluid into the target tissue based on the determined pressure and the determined volume.

18 Claims, 3 Drawing Sheets

(51) Int. Cl.
*A61M 5/172* (2006.01)
*A61M 5/20* (2006.01)
*G06F 19/00* (2018.01)

(52) U.S. Cl.
CPC ........... *A61M 5/20* (2013.01); *G06F 19/3468* (2013.01); *A61M 2205/18* (2013.01); *A61M 2205/33* (2013.01); *A61M 2205/3337* (2013.01); *A61M 2205/3344* (2013.01); *A61M 2205/3379* (2013.01); *A61M 2205/50* (2013.01); *A61M 2205/502* (2013.01); *A61M 2205/52* (2013.01)

(56) References Cited

U.S. PATENT DOCUMENTS

| | | |
|---|---|---|
| 2013/0041258 A1 | 2/2013 | Patrick et al. |
| 2014/0012226 A1* | 1/2014 | Hochman ............ A61M 5/168 604/506 |

FOREIGN PATENT DOCUMENTS

| | | | |
|---|---|---|---|
| WO | 9952572 A1 | 10/1999 | |
| WO | 9952575 A1 | 10/1999 | |
| WO | WO 9952575 A1 * | 10/1999 | .......... A61M 5/1456 |
| WO | 2004075954 A2 | 9/2004 | |
| WO | 2007024399 A2 | 3/2007 | |

* cited by examiner

REGIONAL ANAESTHESIA INJECTION APPARATUS

The present invention relates generally to method and apparatus for the control of devices for performing regional anaesthesia.

Regional anaesthesia is used to block the sensation in a specific part of a patient's body during and after surgery. It offers numerous advantages over conventional general anaesthesia, including faster recovery time, fewer side effects, and a dramatic reduction in post-surgical pain.

The result of an injection of a regional anaesthetic agent is dependent on the location at which the fluid is injected. For example, when the needle enters a nerve it can cause unnecessary pain and damage that may lead to disability.

Embodiments of the disclosure relate to methods and apparatus for controlling an injection based on both the injection pressure and the injection volume to limit the injection of fluid into tissues outside of the target area.

The disclosure is explained, by way of example only, with reference to the accompanying drawings, in which.

It is a problem that needles may move during injections and hit and/or damage a nerve.

The present disclosure provides methods and apparatus for controlling an injection based on a change in injection pressure with respect to a volume of the injection. A controller compares injection pressure and injection volume to stored pressure-volume data, and controls the injection based on this comparison.

If movement of a needle during an injection that begins in one tissue causes the needle to inject fluid into a different tissue the controller is configured detect the change in tissue compliance associated with this movement based on the change in pressure associated with injecting a given volume of fluid. For example, the controller may be configured to obtain a plurality, for example a series, of pressure data associated with a corresponding plurality of injection volume data. The controller can then determine, based on comparing this data with stored data, whether to trigger an alert, for example by sending a signal for controlling the injection, for example by controlling the injector. The stored data may comprise pressure-volume data characteristic of at least one selected tissue type, such as soft tissue or nerve tissue. The series of pressure-volume data obtained by the controller, and the stored data, may each comprise a pressure-volume data set.

Figure 1:
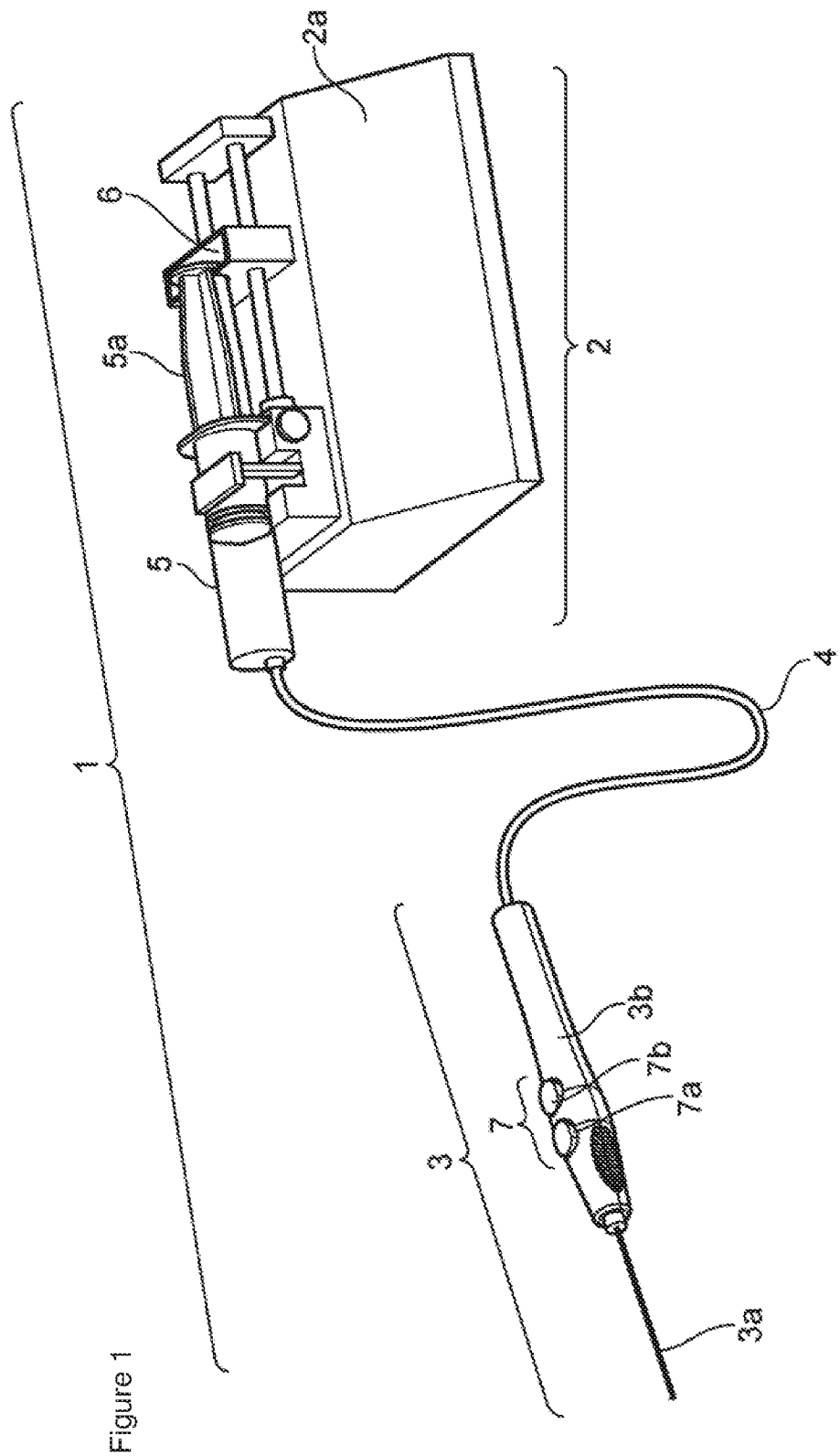
FIG. 1 shows a schematic illustration of an injector.

FIG. 1 shows one example an injector device 1 for performing regional anaesthesia. Embodiments of the present disclosure may be used with this, and other, injection apparatus, and may for example be coupled to control this injector device 1. The injector device 1 illustrated in FIG. 1 comprises an infusion device 2, which is in fluid connection with a regional anaesthetic needle 3 by means of a feed tube 4.

The regional anaesthetic needle 3 has a distal end that is a hollow hypodermic needle 3a that inserts into a patient, and also a proximal end that comprises a needle hub 3b. The length and gauge of the hypodermic needle 3a will depend on the procedure and patient. The feed tube 4 is removably or permanently secured to the needle hub 3b via a Luer connection. The infusion device 2 comprises a housing 2a that holds a fluid provider 5 comprising a reservoir for holding a local anaesthetic. The fluid provider also comprises plunger 5a adapted to push fluid out of the reservoir 5a under the control of a mover 6, such as a motor. The mover 6 is operable to depress or retract the plunger 5a, thereby allowing the fluid provider to provide a selected volume of injection at a selected pressure. When the plunger 5a is depressed by the mover 6, the local anaesthetic is forced out of the fluid provider 5, through the feed tube 4 and into the regional anaesthetic needle 3 so that it may be injected into the patient. The process is reversed when the plunger 5a is withdrawn by the mover 6. The delivery rate of the fluid provider 5 can be readily adjusted. The fluid provider may comprise a syringe, pump, or bellows. In some embodiments the reservoir may comprise fluid that is held at a selected pressure, and the plunger may be replaced by a regulator valve or other fluid flow control device. It will be appreciated that other fluid providers may be used.

Two pushbutton switches 7a 7b may be positioned on the needle hub 3b that can each be in a raised or depressed position. In this embodiment, the pushbuttons 7a 7b are biased in the raised position. Depression of the first pushbutton switch 7a sends a control signal, for example a wireless signal, to the infusion device 2 which triggers the mover 6 to depress the plunger 5a. Depression of the second pushbutton 7b switch sends a control signal, for example a wireless signal, to the infusion device 2 which triggers the mover 6 to retract the plunger 5a. In order to prepare the device 1 for infusion, the syringe 5 is filled with local anaesthetic and the plunger 5a is fully retracted. The first pushbutton switch 7a is then depressed until the first drop of liquid is observed on the tip of the hypodermic needle 3a. The first pushbutton switch 7a is then released.

In use, the clinician can control the flow of the local anaesthetic through the regional anaesthetic needle 3 by simply pressing on the pushbutton switches 7a 7b. Infusion can be activated by depressing the first pushbutton 7a so as to deliver the local anaesthetic to the intended destination. Aspiration can be activated by depressing the second pushbutton 7b so as to allow for visual inspection of the withdrawn liquid in order to reduce the risk of accidental intravenous injection of the local anaesthetic. The flow rate and/or pressure can vary linearly with the amount of depression of, or force applied to, the pushbutton switches 7a 7b. The pushbutton switches 7a 7b may simply activate flow of the local anaesthetic at a flow rate and/or pressure that have been preselected by the clinician.

An injection volume determiner 16 according to the present disclosure can be coupled to determine the volume of fluid that has been injected, for example based on sensing the flow rate, or simply based on a measurement of the movement of the plunger. An injection pressure determiner 20 can be coupled to sense the fluid pressure of the injection, for example based on sensing the pressure in the fluid that is to be injected, for example based on sensing a pressure of the fluid provider 5 for example mechanical pressure applied by the mover to the plunger, for example based on sensing the fluid pressure in the fluid reservoir, or the feed tube, or the needle.

An injection controller is coupled to receive pressure and volume signals from the injection pressure determiner 20 and the volume determiner 16, and is configured to control injection of fluid by the injector device 1 based on these signals. This may be done, for example by triggering an alert, for example such as an audible or visible alarm, and/or such as by sending a signal to control the injection, for example by controlling the mover, or the plunger, or by controlling flow out of the reservoir, for example by restricting flow along the feed tube or into the needle.

Figure 2:
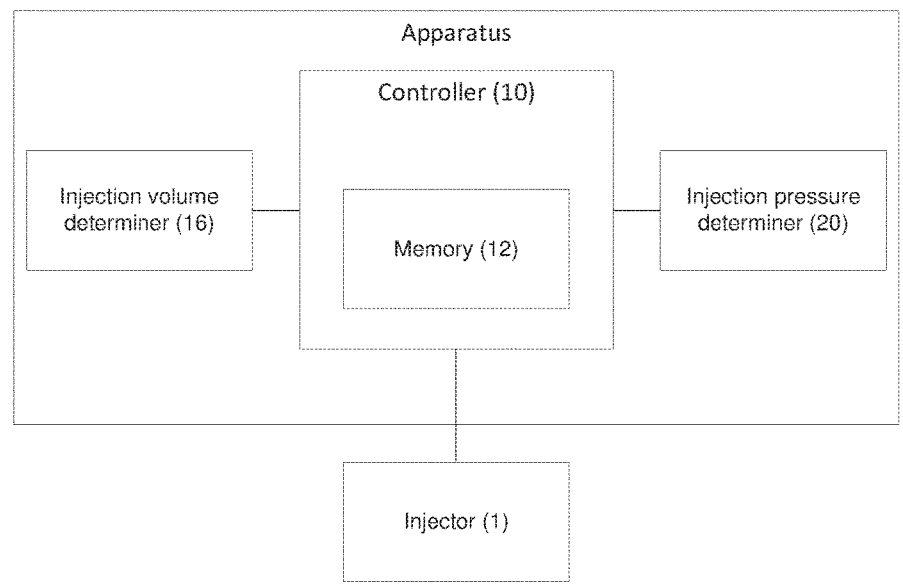
FIG. 2 shows a schematic diagram of an apparatus for controlling an injector.

FIG. 2 shows a schematic diagram of an injection controller adapted to control an injection from a medical or surgical injection device such as that described above with reference to FIG. 1.

The apparatus of FIG. 2 is coupled to control an injector 1 and comprises an injection volume determiner 16, an injection pressure determiner 20, and a controller 10. The controller 10 comprises a memory 12.

The controller 10 is coupled to the injection volume determiner 16, the injection pressure determiner 20, and the injector 1.

The injector 1 is operable to provide an injection of a selectable volume of a regional anaesthesia fluid at a selectable injection pressure, and is operable to be controlled by the controller 10. The injection pressure determiner 20 is configured to sense a fluid pressure in an injection fluid flow path of the injector 1 when fluid is actually injected into tissue. The injection volume determiner 16 is configured to determine a volume of injection fluid that has been provided from the injector 1. The back-pressure from the tissue, and hence the pressure sensed by the pressure determiner 20 may depend upon the volume of fluid that has been injected into the tissue (and perhaps on the volume flow rate of the fluid into the tissue). This may be characteristic of the compliance of the tissue into which fluid is to be injected.

The pressure-volume characteristic may also vary according to site of the injection, for example, an injection into an interscalene site may have a different pressure-volume characteristic to an injection into an axillary site.

The controller 10 is configured to obtain a pressure signal from the injection pressure determiner 20 and to obtain a volume signal from the injection volume determiner 16. The controller 10 is operable to determine the pressure of the injection as a function of the volume of the injection based on these signals. The controller 10 is also configured to store pressure-volume data corresponding to the expected compliance of the tissue receiving the fluid and/or site of injection in the memory 12.

The controller 10 is further configured to compare the obtained pressure and volume signals to stored pressure-volume data, and to determine based on this comparison whether the change in pressure with respect to volume is within an expected bound. A change in pressure with respect to volume outside the expected bound may indicate that the injection that may harm the patient. The controller 10 may be configured to send a signal to the injector 1 based on this determination.

For example, the controller 10 may be configured to compare the change in pressure with respect to volume to the stored pressure-volume data, and to determine whether the difference between the change in pressure with respect to volume and the stored pressure-volume data is greater than a threshold data. The controller 10 is configured to trigger an alert, which may control the injection, in the event that this difference is greater than this threshold data.

In use, a clinician begins an injection into a tissue, and as fluid flows out of the injector 1, the injection volume determiner 16 determines the volume of fluid passed from the injector 1 towards the tissue, and the injection pressure determiner 20 senses the pressure in this injection fluid as the injection proceeds.

The controller 10 obtains a pressure signal from the pressure determiner 20 and a volume signal from the volume determiner 16. The controller 10 may determine the pressure of the fluid in various parts of the system based on the pressure signal, for example, the pressure of the fluid in the fluid reservoir, the tip of the needle, and interface between the needle and the fluid reservoir. The controller 10 may then determine the pressure-volume relationship based on these signals and may compare them to stored pressure-volume data. Based on this comparison the controller 10 determines whether to trigger an alert, for example by sending a control signal to control the injector 1.

In some examples the controller 10 is configured to provide a signal to a visual display to plot a pressure vs. volume graph as the injection proceeds, this permits the clinician to monitor the pressure of the injection in relation to the volume of a tissue-enclosed fluid, such as injected local anaesthetic. The controller 10 may be configured to display such a plot in combination with a display based on stored data to enable a clinician to visually compare the pressure-volume characteristic of an injection into a particular tissue type and/or site of injection with an expected characteristic for an injection into tissue of that type and/or site of injection. This can enable the clinician to identify deviation from this expected characteristic, such as that which might occur when a needle begins to inject fluid into a nerve.

For example, if a needle enters a nerve there would be a decrease in tissue compliance resulting in a large spike in measured pressure for a small injection volume. In addition to, or as an alternative to, displaying pressure-volume data, the controller 10 may be configured to detect selected characteristic signal, such as a large increase in the rate of change of pressure with injection volume, and to trigger an alert to stop the injection of fluid.

The controller 10 may comprise stored criteria corresponding to pressure-volume signals characteristic of injections which may harm the patient. The controller 10 may send a signal to the injector 1 based on whether the comparison corresponds to the stored criteria. In this example, the controller 10 makes a comparison to determine the difference between the change in pressure with respect to volume and the stored pressure-volume data. This difference is compared to the stored criteria. Based on whether the difference is outside the stored criteria the controller 10 controls the injection from the injector 1.

Figure 3:
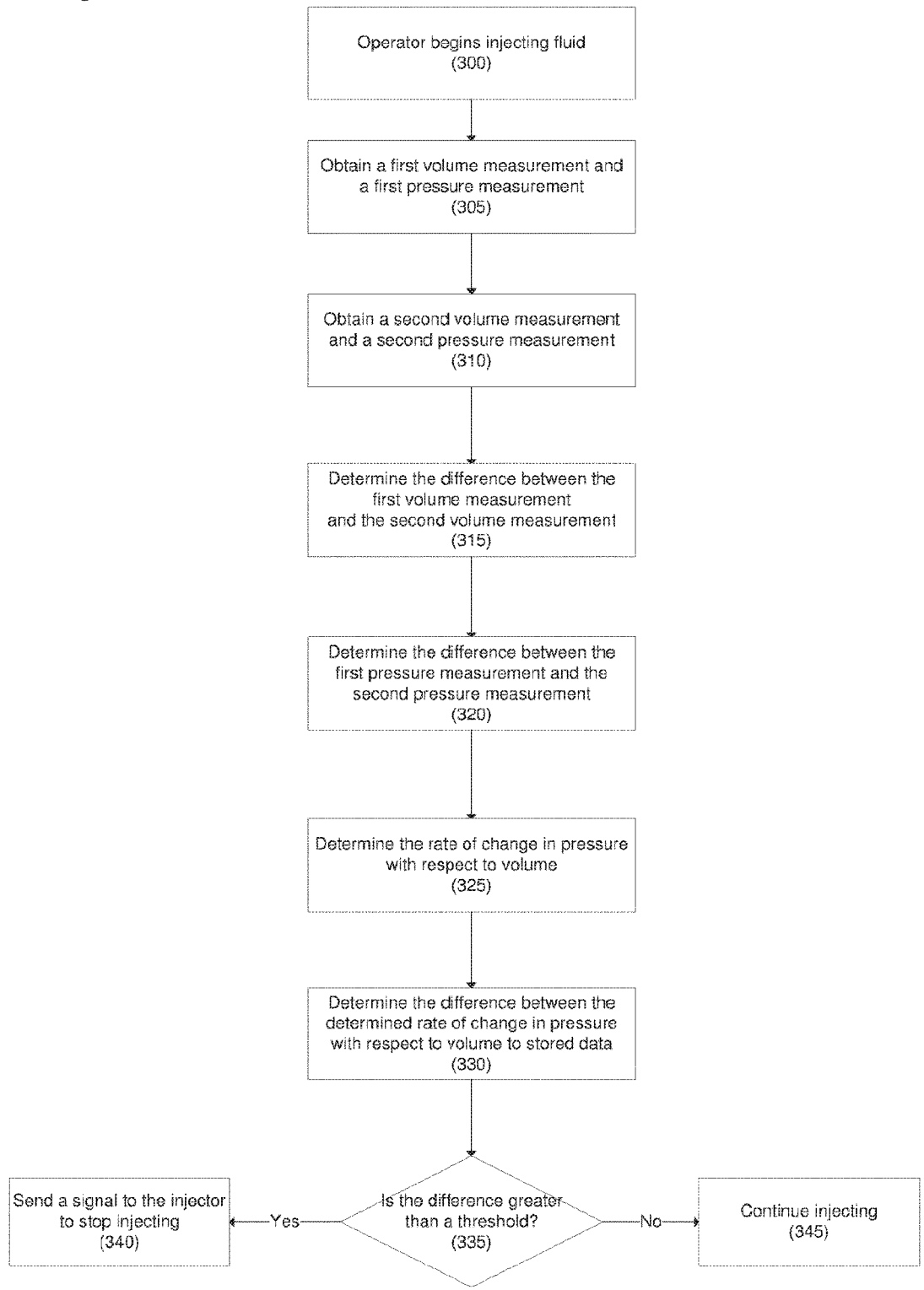
FIG. 3 shows a flow chart of the method of controlling the injection of fluid according to measurements of the volume and pressure.

FIG. 3 shows a flow chart illustrating the control of the injection of fluid into a tissue from a measurement of a first pressure and a first volume at a first point, and a measurement of a second pressure and a second volume at a second point.

The operator begins to inject fluid into the patient, 300. Upon commencing injection into the patient the controller 10 obtains a first volume measurement from the injection volume determiner 16 and obtains a first pressure measurement from the injection pressure determiner 20, 305. The controller 10 subsequently obtains a second volume measurement from the injection volume determiner 16 and obtains a second pressure measurement from the injection pressure determiner 20, 310.

Upon obtaining the first volume measurement and the second volume measurement, the controller 10 determines the change in volume. The first volume measurement corresponds to the conditions of the fluid in the injector 1 at a first point and the second volume measurement corresponds to the conditions of the fluid in the injector 1 at a second point. The controller 10 determines the change in volume from the difference between the first volume measurement and the second volume measurement, 315.

The controller 10 determines the change in pressure from the first pressure measurement and second pressure measurement. The first pressure measurement corresponds to the conditions of the fluid in the injector 1 at the first point and the second pressure measurement corresponds to the conditions of the fluid in the injector 1 at the second point. The controller 10 determines the change in pressure from the difference between the first pressure measurement and the second pressure measurement, 320.

The rate of change in pressure with respect to volume is calculated from the difference between the first pressure measurement and second pressure measurement and the difference between first volume measurement and second volume measurement, 325. The change in the conditions of the fluid during the injection process is determined from the measurement of the volume and the pressure at the first point and the measurement of the volume and the pressure at the second point. The rate of change in pressure with respect to volume of the injection fluid therefore corresponds to the rate of change in the conditions of the fluid during the injection process.

The determined rate of change in pressure with respect to volume is compared to a stored data, 330. The controller 10 compares the difference between the determined rate of change in pressure with respect to volume to a stored data, 335. The difference is compared to a threshold and when the difference is greater than the threshold the controller 10 controls the injection to stop injection of fluid, 340. If the controller 10 determines the difference is less than the threshold the injector 1 continues to inject fluid, 345.

The relationship between the injection pressure and injection volume may be dependent on the injector 1 as well as the compliance of the tissue receiving the fluid and the injection site. A flush procedure of the injector 1 injects fluid from the injector 1 into a medium of known pressure. The medium of known pressure may be a reservoir of fluid at standard atmospheric pressure, for example, a room comprising a reservoir of air at room pressure. The compliance of the injection fluid during the flush procedure is determined and compared to a stored compliance, and based on this comparison the controller 10 may determine calibration data for the injector 1.

The controller 10 controls the injection of fluid based on a comparison to a stored data. The stored data may correspond to an expected compliance of the tissue or the injection site, this expected compliance may be dependent on the patient. For example, the compliance of soft tissue surrounding a nerve varies according to certain attributes, i.e., the age of a patient or the patient's BMI. In one example, the controller 10 receives an input according to one or more characteristics of the patient and, according to this input, selects a stored data corresponding to one or more characteristics of the patient from the memory 12. Selecting the stored data corresponding to the patient reduces the error due to patient variation, allowing a more accurate determination of whether the change in pressure with respect to volume is such that the patient may be harmed.

The controller 10 may also be operable in an aspiration mode. Aspiration to aspirate fluid from the tissue prior to injection is well known in the field. The controller 10 may control the injection based on a comparison of the reduction in pressure during aspiration to a selected threshold value. For example, the controller 10 may send a signal to the injector 1 to inhibit injection in the event that the reduction in pressure is less than a selected threshold value.

The controller 10 may determine a maximum injection volume based on a characteristic of the patient and the injection site. For example, the maximum injection volume may be dependent on the patient's weight, the patient's height, the patient's BMI, and/or the injection site.

In one example the controller 10 determines a pressure-volume data set corresponding to the fluid in the injector 1. The volume of fluid injected is dependent on the pressure applied to the fluid in the injector 1. The pressure of the fluid is related to the volume of fluid injected into the tissue, with an increase in fluid pressure required to increase the volume of fluid injected into the tissue. The controller 10 determines the pressure-volume data set by obtaining the pressure of the fluid at a plurality of points corresponding to different volumes of fluid injected into the patient.

The stored data may comprise a stored pressure-volume data set. The controller 10 may compare the injection pressure-volume data set to the stored pressure-volume data set. During this comparison the controller 10 determines the difference between the injection data set and the stored data set. The difference is compared to one or more set conditions, and the controller 10 controls the injector 1 based on a comparison of the difference and the one or more set conditions. The set conditions may be a threshold data, for example, in response to the controller 10 determining the difference between the injection data set and the stored data set is greater than the threshold data the controller 10 sends a signal to stop further injection.

The comparison of the injection pressure-volume data set to the stored pressure-volume data set by the controller 10 may be made at a plurality of injection volumes. Based on this comparison the controller 10 determines the change in the difference between the injection pressure-volume data set and the stored pressure-volume data set. This change is compared to a set data and the controller 10 controls the injector 1 based on this comparison. For example, the rate of change of the difference between the determined pressure-volume data set and the stored pressure-volume data set with respect to injection volume can be compared to a stored data. The divergence of the injection pressure-volume data set from the selected stored pressure-volume data set at a rate greater than the set data may indicate that a different tissue or injection site is receiving the fluid from the injector 1. For example, a threshold rate corresponding to a rate of change that may be harmful is stored in the controller 10. In response to the controller 10 determining the difference is increasing at a rate greater than a threshold rate a signal is sent to the injector 1 to stop further injection.

The controller 10 may also determine the rate of change of the change in pressure with respect to volume, and compare this rate of change to a set data. A sudden increase in the change in pressure with respect to volume may indicate that the fluid is being received by another tissue or injection site. Based on this comparison the controller 10 controls the injection. For example, the set data may correspond to the rate of change of the change in pressure with respect to volume that may be harmful to the patient, and in response to the rate of change exceeding the set data the controller 10 may send a signal to the injector 1 to stop injecting.

In another example, the determined pressure-volume data is fitted to a plurality of stored pressure-volume data by the controller 10. Based which of the stored data sets providing a best fit to the data, the controller 10 determines an output to the injector 1. For example, a plurality of pressure-volume data sets are stored in the memory 12 of the controller 10. One or more of the stored pressure-volume data sets correspond to an injection that may harm the patient. The fitting parameters of the determined pressure-volume data set for a plurality of stored pressure-volume data sets may be determined by the controller 10. The controller 10 may send a signal to the injector 1 to cease injecting based on whether the determined pressure-volume is a best fit to a stored pressure-volume data set corresponding to an injection that may harm the patient.

The injector 1 may comprise a pump and a reservoir. In this example the injector 1 pumps the injection fluid from the reservoir to into the patient and the controller 10 controls the output of the pump based on the pressure of the fluid output from the pump and the volume of fluid pumped. In other examples, the injector 1 comprises a mechanical injector where the operator continues to inject fluid based on an output from the controller 10.

In the examples described above the controller 10 is configured to obtain a pressure signal and obtain a volume signal. The controller 10 may obtain the pressure signal from a memory of the pressure determiner 20 and obtain the volume signal from a memory of the volume determiner 16. The controller 10 may also obtain the pressure signal by receiving a signal from the pressure determiner 20 and the volume signal by receiving a signal from the volume determiner 16.

In the examples described above the pressure determiner 20 determines the pressure of the injection fluid. The pressure may be determined from a measurement of a compressive force or tensile force on the plunger. The injection pressure may be determined using a pressure sensor coupled to the injection fluid, from a measurement of the fluid carrier and/or a measurement of the tissue receiving the fluid. The pressure sensor may comprise a capacitive pressure sensor, a piezoresistive strain gauge, an electrical resistance strain gauge, electromagnetic sensor, piezoelectric sensor, potentiometer, a resonant frequency pressure sensor, and/or a thermal conductivity pressure sensor.

In the examples described above the volume determiner 16 determines the injection volume. The volume determiner 16 may comprise a volume sensor, for example a sensor configured to determine the change in volume of fluid in the reservoir, for example based on reservoir volume, for example a flow meter, a level sensor on the fluid reservoir, the change in position of the plunger, and/or based on integrating the rate of movement of a plunger reducing the volume of fluid in the reservoir. The movement of the plunger may be determined using a linear potentiometer, and/or the number of steps made by a stepper motor controlling the position of the plunger.

The flow meter described above may measure the flow rate from the rotation of a turbine blade, using an electromagnetic flow meter, an ultrasonic flow meter, and/or via an optical measurement. The flow rate may also be determined from the speed of a motor used to pump the fluid.

In the examples described above the injector 1 may be calibrated by measuring the compliance during an initial flush procedure. The injector 1 may also be calibrated using electronic mechanism or a coded connection mechanism. The calibration of the controller 10 may be determined using an algorithm to determine the pressure drop during injection with respect to the type of feed tube, the length of the feed tube, and/or the type of needle.

The controller 10 may be connected to an injector 1 with a predetermined property and the controller 10 may be calibrated based on the predetermined property. The injector 1 may also comprise an identification means, wherein the controller 10 may determine one or more properties of the injector 1 based on the identification means and may be calibrated based on the one or more properties.

The injector 1 may comprise a memory 12, wherein the controller 10 receives one or more properties of the injector 1 based on data stored in the memory 12. For example, the injector 1 has stored calibration data, usage history data, and/or data based on the condition of the injector 1. The data based on the condition of the injector 1 may include an expiry date of the injector 1.

In the above examples the controller 10 is calibrated based on the injector 1. The injector 1 described above includes the needle, the reservoir and feed tube. The controller 10 may therefore be calibrated based on an individual component of the injector or the complete injector 1.

To the extent that certain methods may be applied to the living human or animal body, it will be appreciated that such methods may not provide any surgical or therapeutic effect. In addition, it will be appreciated that such methods may be applied ex vivo, to tissue samples that are not part of the living human or animal body. For example, the methods described herein may be practices on meat, tissue samples, cadavers, and other non-living objects.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

In some examples, one or more memory elements can store data and/or program instructions used to implement the operations described herein. Embodiments of the disclosure provide tangible, non-transitory storage media comprising program instructions operable to program a processor to perform any one or more of the methods described and/or claimed herein and/or to provide data processing apparatus as described and/or claimed herein.

The activities and apparatus outlined herein may be implemented with fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic, software, code, electronic instructions, flash memory, optical disks, CD-ROMs, DVD ROMs, magnetic or optical cards, other types of machine-readable mediums suitable for storing electronic instructions, or any suitable combination thereof.

The invention claimed is:

1. A regional anaesthesia injection apparatus comprising:
   an injection volume determiner configured to determine a volume of a regional anaesthetic injection into a target tissue;
   an injection pressure determiner configured to determine a pressure of the injection; and
   a controller coupled to the injection volume determiner and to the injection pressure determiner and configured to provide an injection signal to control injection of fluid into the target tissue based on the determined pressure and the determined volume, wherein the controller is configured to obtain a plurality of injection pressure signals and a corresponding plurality of injection volume signals to determine a change of injection pressure with respect to injection volume wherein the controller is configured to obtain a first change of injection pressure with respect to injection volume, and a second change of injection pressure with respect to injection volume, and to provide an injection signal based on, a comparison of:
   (a) the difference between the first change and the second change, with
   (b) a stored signal,
   wherein the stored signal is characteristic of at least one tissue type.

2. The apparatus of claim 1, wherein the injection signal is provided in the event that the difference between a determined pressure-volume characteristic, and a stored pressure-volume characteristic is greater than a threshold level.

3. The apparatus of claim 1, wherein the injection signal is provided in the event that the difference between a determined pressure-volume characteristic, and a stored pressure-volume characteristic increases at a rate that is greater than a threshold rate.

4. The apparatus of claim 1 wherein the stored signal comprises: a stored characteristic associated with at least one of a body mass index and an injection site, an expected compliance of the at least one tissue type, and the apparatus comprises a control interface configured to enable a user to select a body mass index, an injection site, or a tissue type, and the controller is configured to perform the comparing based on the selected body mass index, injection site, or tissue type.

5. The apparatus of claim 1 comprising a display interface configured to provide a signal to a display for providing a visual display based on the determined injection pressure and injection volume.

6. The apparatus of claim 5 wherein the display interface is further configured to provide a signal to a display for displaying a stored pressure-volume characteristic.

7. The apparatus of claim 1 comprising a fluid provider arranged to provide regional anaesthetic for injection.

8. The apparatus of claim 7 wherein the fluid provider comprises a reservoir for holding the regional anaesthetic and a pump operable to pressurise the fluid for injection.

9. The apparatus of claim 8 wherein the controller is configured to provide the injection signal to control the pump.

10. The apparatus of claim 7 wherein the fluid provider comprises a syringe.

11. The apparatus of claim 1, wherein the controller is configured to selectively enable, or inhibit, the injector of the regional anaesthetic fluid based on the injection signal.

12. The apparatus of claim 1, wherein the controller is configured to determine an injection volume of the regional anaesthetic based on stored characteristics associated with at least one of a body mass index, an injection site, and a tissue type.

13. The apparatus of claim 1, wherein the controller is operable in an aspiration mode, prior to commencing injection to identify a reduction in pressure associated with attempting to aspirate a volume of fluid from tissue, and to provide the injection signal to control the injection only in the event that the reduction in pressure exceeds a selected threshold value associated with the volume.

14. A regional anaesthesia injection data controller configured to:
   obtain an injection volume signal indicating the volume of a regional anaesthetic injection into a target tissue;
   obtain an injection pressure signal indicating a pressure of the injection; and
   to provide an injection signal to control injection of regional anaesthetic into the target tissue based on the injection pressure signal and the injection volume signal, wherein the regional anaesthesia injection data controller is configured to:
   determine, from the injection volume signal and the injection pressure signal, a first change of injection pressure with respect to injection volume, and a second change of injection pressure with respect to injection volume and the injection signal is provided based on a comparison of a change of injection pressure with respect to injection volume with stored data, wherein the stored data comprises data defining pressure-volume characteristics of at least one tissue type.

15. The apparatus of claim 14, wherein the stored data comprises a plurality of data defining a pressure-volume characteristic.

16. The apparatus of claim 15 comprising a data store storing a plurality of pressure-volume characteristics, wherein the controller is configured to select one of the stored pressure-volume characteristics and to provide the injection signal based on a comparison with one of the stored characteristics.

17. A tangible, non-transitory, computer readable medium storing computer readable program instructions operable configured, when executed, to program a processor to provide a data controller according to claim 14.

18. A regional anaesthesia injection apparatus comprising:
   an injection volume determiner configured to determine a volume of a regional anaesthetic injection into a target tissue;
   an injection pressure determiner configured to determine a pressure of the injection; and
   a controller coupled to the injection volume determiner and to the injection pressure determiner,
   wherein the controller is configured to obtain a plurality of injection pressure data and a corresponding plurality of injection volume data to determine a rate of change of injection pressure with respect to injection volume, and
   configured to provide an injection signal to control injection of fluid into the target tissue based on a comparison of: (a) the rate of change of injection pressure with respect to injection volume, with (b) a threshold characteristic of nerve tissue.

* * * * *